US010092592B2

(12) United States Patent
Tan et al.

(10) Patent No.: US 10,092,592 B2
(45) Date of Patent: Oct. 9, 2018

(54) APPLICATION OF CYCLIC DINUCLEOTIDE (CGAMP) IN ANTI-TUMOR FIELD

(71) Applicant: FUDAN UNIVERSITY, Shanghai (CN)

(72) Inventors: Xiangshi Tan, Shanghai (CN); Tiejun Li, Shanghai (CN); Qiming Xu, Shanghai (CN); Jie Pan, Shanghai (CN); Yaocheng Rui, Shanghai (CN); Hao Cheng, Shanghai (CN); Yuefan Zhang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 15/304,924

(22) PCT Filed: Apr. 20, 2015

(86) PCT No.: PCT/CN2015/076961
§ 371 (c)(1),
(2) Date: Oct. 18, 2016

(87) PCT Pub. No.: WO2015/161762
PCT Pub. Date: Oct. 29, 2015

(65) Prior Publication Data
US 2017/0196902 A1    Jul. 13, 2017

(30) Foreign Application Priority Data
Apr. 21, 2014   (CN) .......................... 2014 1 0158564

(51) Int. Cl.
A01N 43/04     (2006.01)
A61K 31/70     (2006.01)
A61K 31/7084   (2006.01)
A61K 31/7064   (2006.01)
A61K 31/708    (2006.01)
A61K 31/7076   (2006.01)
A61K 31/706    (2006.01)

(52) U.S. Cl.
CPC ........ A61K 31/7084 (2013.01); A61K 31/706 (2013.01); A61K 31/708 (2013.01); A61K 31/7064 (2013.01); A61K 31/7076 (2013.01)

(58) Field of Classification Search
None
See application file for complete search history.

(56) References Cited

U.S. PATENT DOCUMENTS 7,569,555 B2   8/2009  Karaolis
7,592,326 B2   9/2009  Karaolis
2013/0330375 A1*  12/2013  Khamar ............. A61K 39/0011
                                                      424/248.1
2015/0010613 A1   1/2015  Dubensky, Jr. et al.

FOREIGN PATENT DOCUMENTS

WO    WO 2013 185052    12/2013

OTHER PUBLICATIONS

Tian et al. Afr. J. Tradit. Complement Altern. Med. (2014), vol. 11(3), pp. 92-96.*
Filderman et al. Cancer Research (1992), vol. 52, pp. 3661-3666.*
Dai et al. Molecular Therapy (2008), vol. 16, pp. 782-790.*
Liu et al. Cancer Gene Therapy (2002), vol. 9, pp. 100-108.*
Higano et al. Cancer (2008), vol. 113, pp. 975-984.*
International Search Report regarding International Application No. PCT/CN2015/076961, dated Jul. 22, 2015, 3 pages.
Burdette, D. L, et al., STING is a direct innate immune sensor of cyclic di-GMP, Nature, vol. 478, Oct. 27, 2011, 5 pps.
Davies, B. W., et al., Coordinated regulation of accessory genetic elements produces cyclic di-nucleotides for V. cholera virulence, Cell, vol. 149, Apr. 13, 2012, pp. 358-370.
Diner, E. J., et al. The innate immune DNA sensor cGAS produces a noncanonical cyclic dinucleotide that activates human STING, Cell Reports, vol. 3, May 30, 2013, pp. 1355-1361.
Gao, P., et al., Cyclic [G2',5')pA(3',5') is the metazoan second messenger produced by DNA-activated cyclic GMP-AMP synthase, Cell, vol. 153, May 23, 2013, pp. 1094-1107.
Zhang X., et al., Cyclic GMP-AMP containing mixed phosphodiester linkages is an endogenous high-affinity ligand for STING, Molecular Cell, vol. 51, Jul. 25, 2013, pp. 226-235.

* cited by examiner

Primary Examiner — Patrick T Lewis
(74) Attorney, Agent, or Firm — Foley & Lardner LLP

(57) ABSTRACT

The present invention belongs to the field of medicine technology, particularly relating to an application of cyclic dinucleotide (cGAMP) in tumor treatment. Researches carried out in the present invention show that, cGAMP can inhibit growth of many types of tumor cells, with remarkable anti-tumor effect, thus, it can be used in preparation of anti-tumor drugs; and the prepared anti-tumor drugs have low toxicity and favorable effect. Proved by a subcutaneous tumor model in nude mice, cGAMP has a remarkable inhibition effect on tumors of human gastric carcinoma cell line MNK-45, human lung adenocarcinoma cell line A549, human colorectal carcinoma cell line Lovo, human hepatocellular carcinoma cell line SMMC-7721, human prostatic carcinoma cell line PC-3 and human pancreatic carcinoma cell SW1990, which are subcutaneously implanted in nude mice, and also proved by animal acute toxicity experiment. cGAMP has a relatively low acute toxicity, therefore and may be used for preparing anti-tumor drugs.

19 Claims, No Drawings

APPLICATION OF CYCLIC DINUCLEOTIDE (CGAMP) IN ANTI-TUMOR FIELD

TECHNICAL FIELD

The present invention belongs to the field of medicine technology, and more particularly, relates to an application of cyclic dinucleotide (cGAMP) in anti-tumor field and in preparation of anti-tumor drugs.

BACKGROUND

Tumor is one of the major diseases that seriously endanger human life and health, and it is the abnormal proliferation and differentiation of cells. Experts of WHO predict that in 2020 the global population of cancer incidence will reach 20 million, the death toll will reach 12 million, and the cancer will become the number one killer of human beings in this century and the most serious threat to human survival. Incidence and mortality rates of lung cancer, colorectal cancer, gastric cancer and liver cancer rank in the top five positions among all types of malignant tumors.

According to data from "2012 Chinese Cancer Registry Annual Report", released by the National Cancer Registry, new tumor cases for each year is about 3,120,000, an average of 8, 550 people per day, 6 people per minute in the country are diagnosed with cancer. Lung cancer, gastric cancer, colorectal cancer, liver cancer and esophageal cancer, are ranking in the top five in the national malignant tumor incidence. With the increase of incidence and mortality of malignant tumor, the demand for treatment of malignant tumor is increasing.

Chemotherapy is one of the effective methods for treatment of tumor. Basically, the mechanism of traditional chemotherapy drugs is preventing synthesis of deoxyribonucleic acids (DNA), ribonucleic acids (RNA) or proteins, or directly impacting on these macromolecules, thereby inhibiting the proliferation of cancer cells, then to death. Some drugs are also capable of inhibiting tumor growth by altering the balance of hormones in the human body. At present, anti-tumor drugs have been developed into 6 categories: anti-metabolism drugs; alkylating agents; cell toxin antibiotics; plant alkaloids and other natural drugs; antineoplastic hormones; and platinum and other anti-tumor drugs. With the change of clinical treatment models and discovery of some new anticancer drug targets, great changes have taken place in the field of anti-tumor drugs: mechanism of the drugs, has been transformed from traditional nonspecific cytotoxic drugs into noncytotoxic targeted drugs. In anti-tumor drugs approved by FDA in 2012, small-molecule tyrosine kinase inhibitor (TKI) has become the most popular research in the anti-tumor drugs, especially those targeting to multiple targets (about ¾), as of June 2013, the type of TKI approved by US FDA has reached 18. In addition, other drugs having hot mechanisms include immune stimulants, angiogenesis inhibitors, cell cycle inhibitors, immune inhibitors and stimulants, protein kinase inhibitors and the like.

Microbial and viral DNA in the infected mammalian cells can induce endogenous potent immune responses by stimulating interferon secretion. The endoplasmic reticulum (ER) receptor protein (STING) is an essential factor in the immune response to cytosolic DNA. Recent studies show that the cyclized cGMP-AMP dinucleotide synthetase (cGAS) after bonding with DNAs under activation conditions can endogenously catalyze the synthesis of cGAMP. cGAMP is a cytoplasmic DNA sensor, which is used as a second messenger to stimulate the induction of INF-ß by STING, to mediate the activation of TBK1 and IRF-3, and then to start the transcription of INF-ß gene. The recent reports show that, recombinant cGAS can catalyze cyclization of cGMP-AMP dinucleotide GAMP under the DNA binding conditions. The crystal structure of the complex of cGAS bonded with 18 bp dsDNA has also been reported, and a study of cGAMP in antiviral immunity has been confirmed. cGAMP bonded with STING, makes transcription factor IRF3 activated and generates ß interferon.

SUMMARY

The present invention is to provide an application of cGAMP in anti-tumor field.

The present invention also aims to provide an application of cGAMP in the preparation of anti-tumor drugs, to obtain the anti-tumor drugs with low toxicity and favorable effect.

Experimental studies of the present invention show that, cGAMP is capable of inhibiting growth of many types of cancer cells, with a remarkable anti-tumor effect, and may be used for preparing anti-tumor drugs.

In the present invention, the tumors include but are not limited to gastric cancer, lung cancer, colon cancer, liver cancer, prostate cancer, pancreatic cancer and the like.

The present invention also relates to anti-tumor drugs prepared by using cGAMP, and the prepared anti-tumor drugs have a low toxicity and a favorable effect.

DETAILED DESCRIPTION

Hereinafter, the present invention is described in detail with reference to the following embodiments. In the present invention, the following embodiments are merely used for better describing and interpreting the invention, instead of limiting the scope of the present invention.

EXAMPLES

Example 1: Preparation of cGAMP cGAMP (cyclized GMP-AMP), with purity above 98%, was catalytically synthesized by cGMP-AMP dinucleotide synthetase (cGAS), after bonding DNAs under activation conditions, according to the literature method (Pingwei Li, et al., Immunity, 2013, 39(6), 1019-1031).

Example 2: Anti-Tumor Effect of cGAMP (Cyclized GMP-AMP)

Anti-tumor effect of cGAMP (cyclized GMP-AMP) was detected by employing a tumor-bearing mouse model to test inhibition effect of cGAMP on subcutaneously transplanted tumor.

The tested drug:
Name: cGAMP
Character: white powders
Solvent: brine
Preparation method: the test drug was dissolved to obtain a solution having a required concentration with brine before use
Concentration of the tested drug: 1 mg/ml and 4 mg/ml.
Animals: Nude mouse BALB/c, male, with a body weight of 16-18 g, 4-6 weeks old, SPF grade, purchased from SLAC LABORATORY ANIMAL [certification number: SCXK (Shanghai) 2007-0005].

Raising conditions: All the nude mice are free to find food and drink, and are raised at room temperature (23±2° C.) in an experimental animal center of a military medical university of PLA China. Feedstuff and water are treated by high pressure sterilization, and all the experimental feeding processes are of SPF grade.

Dose: cGAMP was injected into abdominal cavities of mice, and two dose groups were set as followed: 10 mg/kg and 40 mg/kg.

Experimental Controls:
Negative control: brine solution
Positive control: 5-fluorouracil (5-FU), with a dose of 20 mg/kg
Administration Method:
Administration route: administration by intraperitoneal injection
Administration frequency: once a day for 14 days
Number of each group of animals: 8
Tumor cell lines: human gastric carcinoma cell line MNK-45, human lung adenocarcinoma cell line A549, human colorectal carcinoma cell line Lovo, human hepatocellular carcinoma cell line SMMC-7721, human prostatic carcinoma cell line PC-3 and human pancreatic carcinoma cell SW1990, purchased from the Cell Bank of the Chinese Academy of Sciences, are included in the above mentioned tumor cell lines.

Main steps of the test. The test mainly comprises the following steps:

1. establishing a tumor-bearing mouse model and allowing intervention, including: cultivating and passaging cells, collecting cells in logarithmic phase, and making into a cell suspension with a concentration of $1.0 \times 10^7$/ml, injecting 0.2 ml of the cell suspension into the nude mice through their right arm armpits to make them get a tumor, and randomly dividing the nude mice into four groups: a negative control which is a group injected with brine through intraperitoneal injection, a 5-FU group which is a group injected with 5-FU through intraperitoneal injection, a cGMP-AMP low-dose group which is a group injected with 10 mg/kg of cGMP-AMP through intraperitoneal injection, and a cGMP-AMP high-dose group which is a group injected with 40 mg/kg of cGMP-AMP through intraperitoneal injection, administrating once a day for 14 days, then killing the nude mice and weighing the wts. Of tumor and calculating a tumor inhibition rate, which is calculated by the following equation: tumor inhibition rate[1−average tumor weight of experimental groups/average tumor weight of A group]×100%, wherein the experimental groups are B, C and D groups; separately establishing 6 subcutaneously implanted tumor models: human gastric carcinoma cell line MNK-45, human lung adenocarcinoma cell line A549, human colorectal carcinoma cell line Lovo, human hepatocellular carcinoma cell line SMMC-7721, human prostatic carcinoma cell line PC-3 and human pancreatic carcinoma cell SW1990, and observing the effect of cGAMP; and 2. allowing statistical analysis: representing the data by x±s, processing the data with a software SPSS-10.0, analyzing by one-way ANOVA, comparing the significance of tumor weight differences among the groups, wherein the level of significance is a=0.05.

Results showed that the nude mice after subcutaneously implanted with tumor cells were successfully prepared into subcutaneously implanted tumor models, both 5-FU and cGAMP could remarkably inhibit tumor growth, after administrating for 14 days, the tumor weights were obviously lower than the negative control (P<0.05, P<0.01), demonstrating that, cGAMP has an anti-tumor effect.

The results were presented in detail by Tables 1-6.

TABLE 1

Effect of cGAMP on subcutaneously transplanted tumor of human gastric carcinoma cell line MNK-45 in nude mice (n = 8, mean ± SD)

| Group | Average Tumor Weight (g) | Average Tumor Inhibition Rate (%) |
|---|---|---|
| Negative control | 2.678 ± 0.226 (g) | — |
| 5-FU group | 0.619 ± 0.214 (g)** | 76.9 |
| cGAMP low-dose group | 1.641 ± 0.175 (g)** | 38.7 |
| cGAMP high-dose group | 1.037 ± 0.198 (g)** | 61.3 |

Post scriptum:
*P < 0.05 vs negative control;
**P < 0.01 vs negative control

TABLE 2

Effect of cGAMP on subcutaneously transplanted tumor of human lung adenocarcinoma cell line A549 in nude mice (n = 8, mean ± SD)

| Group | Average Tumor Weight (g) | Average Tumor Inhibition Rate (%) |
|---|---|---|
| Negative control | 2.837 ± 0.269 (g) | — |
| 5-FU group | 0.843 ± 0.210 (g)** | 70.3 |
| cGAMP low-dose group | 1.562 ± 0.102 (g)** | 44.9 |
| cGAMP high-dose group | 1.151 ± 0.121 (g)** | 59.4 |

Post scriptum:
*P < 0.05 vs negative control;
**P < 0.01 vs negative control

TABLE 3

Effect of cGAMP on subcutaneously transplanted tumor of human colorectal carcinoma cell line Lovo in nude mice (n = 8, mean ± SD)

| Group | Average Tumor Weight (g) | Average Tumor Inhibition Rate (%) |
|---|---|---|
| Negative control | 2.718 ± 0.213 (g) | — |
| 5-FU group | 0.769 ± 0.101 (g)** | 71.7 |
| cGAMP low-dose group | 1.714 ± 0.137(g)** | 36.9 |
| cGAMP high-dose group | 1.204 ± 0.122 (g)** | 55.7 |

Post scriptum:
*P < 0.05 vs negative control;
**P < 0.01 vs negative control

TABLE 4

Effect of cGAMP on subcutaneously transplanted tumor of human hepatocellular carcinoma cell line SMMC-7721 in nude mice (n = 8, mean ± SD)

| Group | Average Tumor Weight (g) | Average Tumor Inhibition Rate (%) |
|---|---|---|
| Negative control | 3.125 ± 0.297 (g) | — |
| 5-FU group | 0.853 ± 0.082 (g)** | 72.7 |
| cGAMP low-dose group | 1.916 ± 0.174 (g)** | 38.7 |
| cGAMP high-dose group | 1.089 ± 0.130(g)** | 65.2 |

Post scriptum:
*P < 0.05 vs negative control;
**P < 0.01 vs negative control

TABLE 5

Effect of cGAMP on subcutaneously transplanted
tumor of human prostatic carcinoma cell line PC-3
in nude mice (n = 8, mean ± SD)

| Group | Average Tumor Weight (g) | Average Tumor Inhibition Rate (%) |
|---|---|---|
| Negative control | 3.068 ± 0.281 (g) | — |
| 5-FU group | 0.728 ± 0.102 (g)** | 76.3 |
| cGAMP low-dose group | 1.467 ± 0.201 (g)** | 52.2 |
| cGAMP high-dose group | 0.932 ± 0.148(g)** | 69.6 |

Post scriptum:
*$P < 0.05$ vs negative control;
**$P < 0.01$ vs negative control

TABLE 6

Effect of cGAMP on subcutaneously transplanted
tumor of human pancreatic carcinoma cell SW1990
in nude mice (n = 8, mean ± SD)

| Group | Average Tumor Weight (g) | Average Tumor Inhibition Rate (%) |
|---|---|---|
| Negative control | 2.957 ± 0.276 (g) | — |
| 5-FU group | 0.685 ± 0.086 (g)** | 76.8 |
| cGAMP low-dose group | 1.631 ± 0.133 (g)** | 44.8 |
| cGAMP high-dose group | 0.964 ± 0.109(g)** | 67.4 |

Post scriptum:
*$P < 0.05$ vs negative control;
**$P < 0.01$ vs negative control Example 3: Study on Acute Toxicity of cGAMP Materials The materials are 20 of ICR mice, which are purchased from SLAC LABORATORY ANIMAL [certification number: SCXK (Shanghai) 2007-0005], are half male and half female, have body weights within 18-22 g, are fed with granular feedstuff and are free to find food and drink.

Methods

The method includes: subjecting the ICR mice to single tail intravenous injection of 10 ml/kg cGMAP based on their body weights, namely 2 g/kg, observing toxic reactions and deaths after administration within 14 days. The results showed that, after the single tail intravenous injection, normal physiological activity was observed. Within 14 days after administration, no death was observed, on the 15th day, all the mice were killed and dissected, and no obvious pathological changes in organs were observed by naked eyes.

Results

The above acute toxicity test results show that the maximum tolerated dose of intravenous injection MTD is not less than 2 g/kg, indicating that the acute toxicity of cGAMP is lower.

What is claimed is:

1. A method for treating a malignant tumor in a subject in need thereof comprising administering to the subject a composition consisting essentially of cGAMP.

2. The method of claim 1, wherein the malignant tumor is a gastric tumor.

3. The method of claim 1, wherein the malignant tumor is a lung tumor.

4. The method of claim 1, wherein the malignant tumor is a colon tumor.

5. The method of claim 1, wherein the malignant tumor is a liver tumor.

6. The method of claim 1, wherein the malignant tumor is a prostate tumor.

7. The method of claim 1, wherein the malignant tumor is a pancreatic tumor.

8. The method of claim 1, wherein the administering is performed systemically.

9. The method of claim 1, wherein the composition is administered daily for 2 weeks or more.

10. The method of claim 1, wherein the treatment results in reduced tumor weight relative to untreated controls.

11. A method for inhibiting tumor growth comprising contacting tumor cells with a composition consisting essentially of cGAMP.

12. The method of claim 11, wherein the tumor cells are selected from the group consisting of gastric carcinoma cells, lung adenocarcinoma cells, colorectal carcinoma cells, hepatocellular carcinoma cells, prostatic carcinoma cells, and pancreatic carcinoma cells.

13. The method of claim 11, wherein the tumor cells are from human gastric carcinoma cell line MNK-45.

14. The method of claim 11, wherein the tumor cells are from human lung adenocarcinoma cell line A549.

15. The method of claim 11, wherein the tumor cells are from human colorectal carcinoma cell line Lovo.

16. The method of claim 11, wherein the tumor cells are from hepatocellular carcinoma cell line SMMC-7721.

17. The method of claim 11, wherein the tumor cells are from prostatic carcinoma cell line PC-3.

18. The method of claim 11, wherein the tumor cells are from pancreatic carcinoma cell line SW1990.

19. A method for treating a malignant tumor in a subject in need thereof comprising administering to the subject a composition consisting essentially of an anti-tumor drug and a pharmaceutically acceptable carrier, wherein the anti-tumor drug comprises cGAMP, and the malignant tumor is a hepatocellular carcinoma or a gastric carcinoma.

* * * * *